(12) United States Patent
Fenner et al.

(10) Patent No.: US 11,189,390 B2
(45) Date of Patent: Nov. 30, 2021

(54) POWER SOURCE AND METHOD OF FORMING SAME

(71) Applicant: Medtronic, Inc., Minneapolis, MN (US)

(72) Inventors: Andreas Fenner, Chandler, AZ (US); Jennifer Lorenz Marckmann, Scottsdale, AZ (US); David A. Ruben, Mesa, AZ (US); James R. Wasson, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/804,163

(22) Filed: Feb. 28, 2020

(65) Prior Publication Data

US 2020/0203034 A1   Jun. 25, 2020

Related U.S. Application Data

(63) Continuation of application No. 15/427,152, filed on Feb. 8, 2017, now Pat. No. 10,580,544.

(60) Provisional application No. 62/431,225, filed on Dec. 7, 2016.

(51) Int. Cl.
| | |
|---|---|
| *G21H 1/12* | (2006.01) |
| *H01L 31/055* | (2014.01) |
| *G21H 1/06* | (2006.01) |
| *A61N 1/39* | (2006.01) |
| *H01L 31/0352* | (2006.01) |
| *A61N 1/378* | (2006.01) |

(52) U.S. Cl.
CPC ............... *G21H 1/12* (2013.01); *A61N 1/378* (2013.01); *A61N 1/3956* (2013.01); *G21H 1/06* (2013.01); *H01L 31/0352* (2013.01); *H01L 31/055* (2013.01); *Y02E 10/52* (2013.01)

(58) Field of Classification Search
None
See application file for complete search history.

(56) References Cited

U.S. PATENT DOCUMENTS

| | | | |
|---|---|---|---|
| 3,706,893 A | 12/1972 | Olsen et al. | |
| 5,082,505 A * | 1/1992 | Cota | G21H 1/12 136/244 |
| 6,304,766 B1 | 10/2001 | Colvin, Jr. | |
| 7,663,288 B2 | 2/2010 | Chandrashekhar et al. | |

(Continued)

FOREIGN PATENT DOCUMENTS

| | | | | |
|---|---|---|---|---|
| DE | 2708825 A1 * | 9/1978 | ....... | G02F 1/133617 |
| GB | 638106 A | 5/1950 | | |

OTHER PUBLICATIONS

DE-2708825-A1, Machine Translation, Hanlet (Year: 1978).*

(Continued)

*Primary Examiner* — Devina Pillay
(74) *Attorney, Agent, or Firm* — Mueting Raasch Group

(57) ABSTRACT

Various embodiments of a power source and a method of forming such power source are disclosed. The power source can include an enclosure, a substrate disposed within the enclosure, and radioactive material disposed within the substrate and adapted to emit radioactive particles. The power source can further include a diffusion barrier disposed over an outer surface of the substrate, and a carrier material disposed within the enclosure, where the carrier material includes an oxide material.

20 Claims, 4 Drawing Sheets

(56) References Cited

U.S. PATENT DOCUMENTS

| | | |
|---|---|---|
| 7,939,986 B2 | 5/2011 | Chandrashekhar et al. |
| 8,017,412 B2 | 9/2011 | Spencer et al. |
| 8,134,216 B2 | 3/2012 | Spencer et al. |
| 8,153,453 B2 | 4/2012 | Spencer et al. |
| 8,487,507 B1 | 7/2013 | Cabauy et al. |
| 8,552,616 B2 | 10/2013 | Prelas |
| 8,802,456 B2 | 8/2014 | Spencer et al. |
| 8,866,152 B2 | 10/2014 | Lal et al. |
| 8,866,245 B2 | 10/2014 | Spencer et al. |
| 8,872,408 B2 | 10/2014 | Zafiropoulo et al. |
| 9,006,955 B2 | 4/2015 | Batchelder |
| 9,183,960 B2 | 11/2015 | Batchelder |
| 9,224,901 B1 * | 12/2015 | Squillante ............... G01T 1/20 |
| 9,266,437 B2 | 2/2016 | Zafiropoulo et al. |
| 9,391,218 B2 | 7/2016 | Gaspari |
| 10,290,757 B2 | 5/2019 | Fenner et al. |
| 2004/0150290 A1 | 8/2004 | Gadeken |
| 2005/0279915 A1 * | 12/2005 | Elofson ............... C09K 11/08 |
| | | 250/205 |
| 2009/0026879 A1 | 1/2009 | Prelas |
| 2011/0100439 A1 | 5/2011 | Clothier et al. |
| 2014/0370332 A1 * | 12/2014 | Cabauy ............... G21H 1/06 |
| | | 429/5 |
| 2015/0279491 A1 | 10/2015 | Fenner et al. |
| 2016/0185081 A1 | 6/2016 | Sandlin et al. |
| 2017/0069775 A1 | 3/2017 | Fenner et al. |

OTHER PUBLICATIONS (PCT/US2017/064875) PCT Notification of Transmittal of the International Search Report and the Written Opinion of the International Searching Authority, dated Feb. 20, 2018, 12 pages.

* cited by examiner

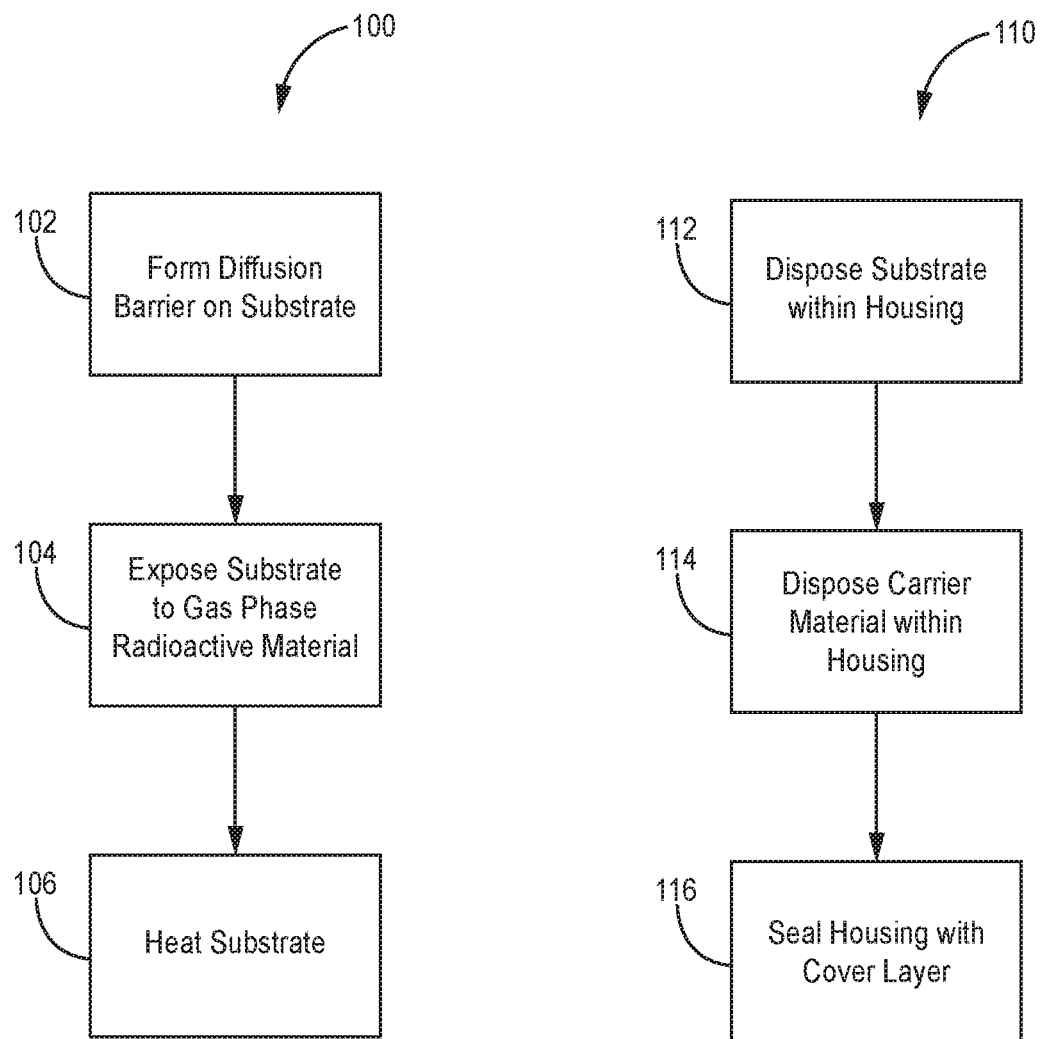

POWER SOURCE AND METHOD OF FORMING SAME

CROSS-REFERENCE TO RELATED APPLICATION

This application is a Continuation of U.S. patent application Ser. No. 15/427,152, filed Feb. 8, 2017, which claims the benefit of the filing date of U.S. Provisional Patent Application No. 62/431,225, filed Dec. 7, 2016, the content of both of which are incorporated herein by reference in their entirety.

BACKGROUND

Power sources such as radiation particle power converters can convert energy from a radioactive source that emits high-energy electrons, e.g., beta particles, into electrical energy. The power converter can directly convert the energy of the high-energy electrons to electrical energy, i.e., current, by collecting electron-hole pairs that are formed by the high-energy electrons that are incident upon a semiconductor material of the power converter.

One such direct power source includes a radiation-emitting radioisotope and a plurality of semiconductor substrates. Each of the plurality of semiconductor substrates includes a junction for converting radiation particles to electrical energy, e.g., a p-n junction. The junction collects electron-hole pairs that are created within the semiconductor material caused by interaction between the nuclear radiation particles and the semiconductor material. Specifically, when a radiation particle of sufficient energy is incident upon the semiconductor material, electrons in the semiconductor material are excited into a conduction band of the semiconductor material, thereby creating electron-hole pairs. Electrons formed on an n side of a p-n junction are generally prevented from crossing the p-n junction due to the electric field that is created in a depletion zone, while the corresponding holes are swept across the p-n junction by the electric field. Electrons formed on the p side of the p-n junction are swept across the junction by the electric field while the corresponding holes are prevented from crossing the junction by the electric field. When the semiconductor material is connected to a load, electrons formed on the n side of the junction are swept across the junction from the p side via an anode and through a circuit connected to the power converter. The electrons that flow through the circuit then flow into the p side via a cathode, where they can recombine with holes from the original electron-hole pairs.

Other types of power sources that utilize radiation particles indirectly convert the particles by utilizing a phosphor layer disposed adjacent the radiation particle source. The phosphor absorbs the energy of the radiation particles and emits visible or invisible light, which is absorbed and converted into electricity by a photovoltaic device. While such indirect power sources may initially be less efficient than direct power sources, over time such indirect power sources have a higher efficiency and longer service life than that of at least some of the direct power sources.

SUMMARY

In general, the present disclosure provides various embodiments of a power source and a method of forming such power source. The power source can include an enclosure, a substrate disposed within the enclosure, and radioactive material disposed within the substrate. The power source can also include a diffusion barrier disposed over an outer surface of the substrate, and a carrier material disposed within the enclosure. The radioactive material can be adapted to emit radiation particles. In one or more embodiments, the power source can also include a radiation particle converter that can be adapted to convert one or more radiation particles emitted by the radioactive material into electrical energy. Further, in one or more embodiments, one or more inputs can be provided to the substrate such that at least a portion of the radioactive material diffuses from the substrate and reacts with the carrier material to provide the radioactive particles.

In one aspect, the present disclosure provides a power source that includes an enclosure, a substrate disposed within the enclosure, and radioactive material disposed within the substrate and adapted to emit radioactive particles. The power source further includes a diffusion barrier disposed over an outer surface of the substrate, and a carrier material disposed within the enclosure, where the carrier material includes an oxide material.

In another aspect, the present disclosure provides a power source that includes an enclosure having a housing and a cover connected to the housing such that the enclosure is hermetically sealed, a substrate disposed within the enclosure, and radioactive material disposed within the substrate and adapted to emit radioactive particles. The power source further includes a carrier material disposed within the housing; particle converting material disposed within the housing, where the particle converting material is adapted to convert the radioactive particles emitted by the radioactive material into light; and a photovoltaic device disposed adjacent the enclosure. The photovoltaic device converts at least a portion of the light emitted by the particle converting material that is incident upon an input surface of the photovoltaic device into electrical energy.

In another aspect, the present disclosure provides a power source that includes an enclosure having a housing and a cover connected to the housing such that the enclosure is hermetically sealed, a substrate including a diffusion barrier disposed over an outer surface of the substrate, and radioactive material disposed within the substrate and adapted to emit radioactive particles. The power source further includes carrier material disposed within the housing, and a charge carrier separator disposed within the housing such that radioactive particles emitted by the radioactive material are incident upon the charge carrier separator.

In another aspect, the present disclosure provides a method of forming a power source. The method includes forming a diffusion barrier on a substrate, disposing radioactive material within the substrate, and disposing the substrate within a housing. The method further includes disposing a carrier material within the housing, where the carrier material includes an oxide material; sealing the housing with a cover connected to the housing to form an enclosure; and heating the substrate such that the radioactive material diffuses from the substrate and reacts with the carrier material.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. The term "consisting of" means "including," and is limited to whatever follows the phrase "consisting of" Thus, the phrase "consisting of" indicates that the listed elements are required or mandatory and that no other elements may be present. The term "consisting essentially of" means including any elements listed after the phrase, and is limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIG. 2 is a flow chart of one embodiment of forming a substrate that includes radioactive material disposed therein for use in the power source of FIG. 1.

FIG. 3 is a flow chart of one embodiment of a method of forming a power source.

DETAILED DESCRIPTION

Figure 1:
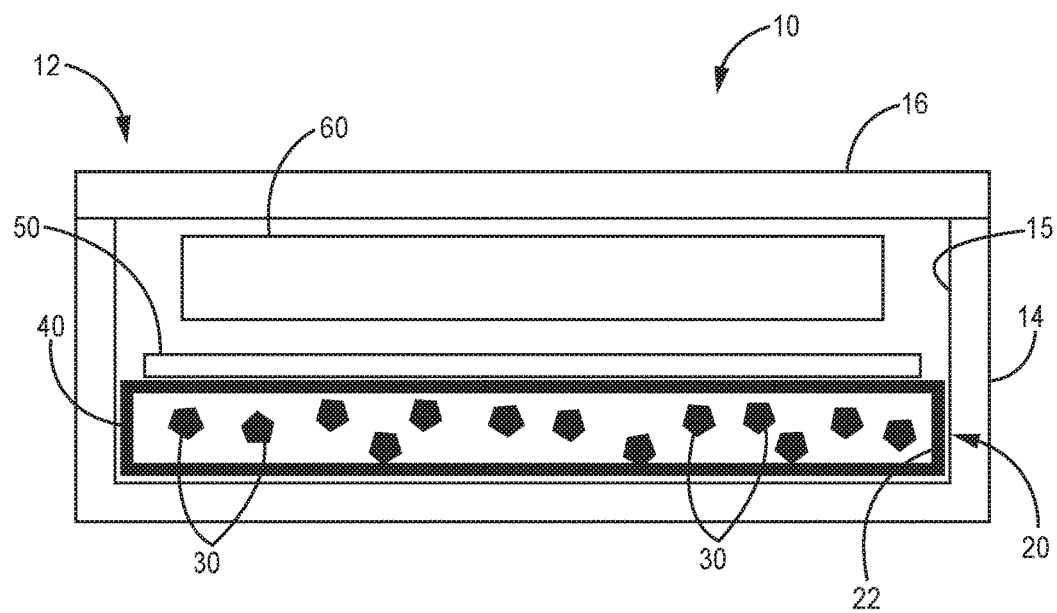
FIG. 1 is a schematic cross-section view of one embodiment of a power source.

In general, the present disclosure provides various embodiments of a power source and a method of forming such power source. The power source can include an enclosure, a substrate disposed within the enclosure, and radioactive material disposed within the substrate. The power source can also include a diffusion barrier disposed over an outer surface of the substrate, and a carrier material disposed within the enclosure. The radioactive material can be adapted to emit radiation particles. In one or more embodiments, the power source can also include a radiation particle converter that can be adapted to convert one or more radiation particles emitted by the radioactive material into electrical energy. Further, in one or more embodiments, one or more inputs can be provided to the substrate such that at least a portion of the radioactive material diffuses from the substrate and reacts with the carrier material to provide the radioactive particles.

Power sources that utilize radioactive particles such as beta particles (i.e., a betavoltaic power source) include radioactive material that decays to provide the radioactive particles. The radioactive material is typically stored in a manner that maximizes the material's storage density while at the same time minimizes losses caused by self-absorption within the material.

For example, betavoltaic power sources rely on beta particles, which are high energy electrons that are emitted from decaying radioactive material. While many beta emitting isotopes of various lifetimes and energies exist, isotopes that have a relatively low mass (to minimize self-absorption) with reasonable half-lives and electron energies of less than what could cause damage in other materials used in the power source, e.g., 100 keV or less, may be preferred. One such isotope is tritium ($^3$H), which is an isotope of hydrogen and has an atomic mass of 3 u, an approximate 12.3 year half-life, and peak energies of 18.6 keV. Tritium, however, is a gas at normal operating temperatures and atmospheric pressures, thereby limiting its useful power density.

Several approaches can be utilized to improve the density of tritium include storing the isotope within a metal, such as titanium, where it is bound as a tritide. Relatively high atomic loading ratios can be achieved with this approach, but such ratios are typically capped at about 1:1 or less to prevent embrittlement. Regardless of loading ratios, a mean free path of beta particles bound in titanium is limited to about 190 nm, with a maximum range of about 1.5 µm for the highest-energy beta particles (at which point they would exit with no remaining energy useful for conversion). This limits the volumetric density of the particle that can exit this material and then be accessible for generating electron-hole pairs that are either collected (for direct converters), or which emit photons when recombined (for indirect converters).

Many other materials have been explored for storage of hydrogen isotopes in hydrogen-powered vehicles, but all have the similar limitation in that they consist of heavier elements, limiting the available beta particles useful for conversion when used with tritium. Mg is currently being studied for use, but it too limits the mean free path, albeit not as much as titanium or other similar elements.

Other compounds that have been considered for hydrogen storage include water, which exhibits some desirable properties. Water includes two hydrogen atoms for each oxygen atom, and has a high decomposition temperature/energy need and a relatively low density. The same compound using the radioactive isotope of hydrogen (tritium), or $T_2O$ (tritium oxide), allows for a mean free path of about 700 nm with a maximum range of 5.5 μm, which is more than 3 times that of titanium.

From a safety perspective, $T_2O$ may be more preferred than metallic-bound tritium. If ingested, $T_2O$ has a biologic half-life of about 10 days, thereby limiting the overall dose of exposure. Metallic bound tritium is likely to remain in place for a long time; therefore, the half-life of the isotope itself is a determining factor of the dose received within the body.

$T_2O$ is not, however, readily available, and, therefore, needs to be synthesized for use. From a manufacturability perspective, it may be preferred that $T_2O$ is synthesized as late in the process as possible. In one or more embodiments of the present disclosure, the $T_2O$ can be synthesized in situ within a hermetically sealed package.

For example, in one or more embodiments, the elements used to form the $T_2O$ can be stored separately and then released in situ. The first element, tritium, can be stored within a material with a very high tritium-to-storage-material ratio, thereby minimizing the overhead of the storage material itself. The storage material can contain the tritium until such time as an external input is provided to cause its release. Typically, this input is in the form of temperature, but other inputs, such as current, vacuum, etc., can also be employed. One such suitable storage material is palladium. Bare palladium, however, will out-diffuse the tritium quite readily over some period of time at ambient atmospheric conditions. To prevent this from occurring, a thin layer (e.g., having a thickness of 10 nm to 50 nm), e.g., of titanium can be deposited on the surfaces of the palladium to serve as a diffusion barrier. In one or more embodiments, titanium naturally forms a thin oxide after exposure to ambient conditions, which can assist in the function of a diffusion barrier. The deposition is generally accomplished by sputtering, but other approaches such as evaporation may be used as well. In one or more embodiments, Atomic Layer Deposition (ALD) may be used to deposit a diffusion barrier such as $TiO_2$ onto the storage material. Other materials and processes may also be utilized to form suitable diffusion barriers.

The second component that can be utilized to form tritium oxide is oxygen. In one or more embodiments, the tritium disposed within the substrate diffuses from the substrate with the provided input and reacts with oxygen, thereby reducing the oxygen source at temperatures around the same, less, or greater than that required to liberate the tritium from the substrate. Suitable oxygen sources include oxides such as palladium oxide (PdO) or silver oxide ($Ag_2O$). These materials are generally in the form of powders, which may be dispersed or deposited within a volume of an enclosure of the power source, but may also be in other forms, such as pellets, slugs, etc. In one or more embodiments, the oxygen source can be a solid material that is oxidized in a structure having a high surface area while occupying a smaller volume (foam, mesh, etc.). The oxygen source may also be deposited onto a high surface area structure and then oxidized in situ or as part of the deposition process.

The radioactive material and the oxygen source can be placed within a housing, which can then be hermetically sealed with a cover. In one or more embodiments, the housing can be sealed with a cover in a low atmospheric, near-vacuum environment. Once sealed, the power source can be heated to a temperature such that the radioactive material diffuses from the substrate and reacts with the oxygen source to form a liquid phase of the radioactive material, e.g., tritium oxide ($T_2O$. In one or more embodiments, the power source can be formed using materials that are hermetic to the tritium oxide but allow any decay products formed by the decay of the radioactive material (e.g., $^3He$) to escape. For example, borosilicate glass or similar materials are known to allow helium diffusion; however, any material that possess these properties, either intrinsically or engineered, may be used for such purpose. In one or more embodiments, the enclosure may be engineered such that it will tolerate the pressure build-up due to the production of the helium, and/or be large enough to contain the material.

Other approaches of generating the radioactive material in a desired phase include injecting gas phase radioactive material and an oxygen source into the sealed enclosure through one or more entry ports, again creating tritium oxide in situ. In one or more embodiments, tritium oxide may be produced offline and utilized in a power source in finished form.

In one or more embodiments, a power source that includes a substrate and oxygen source can utilize a two-step process of converting radiation particles to electrical energy. For example, beta energy released by a radioactive material can be converted to electromagnetic radiation, e.g., light. The electromagnetic radiation can then be converted into electrical energy (e.g., electrical current) using, e.g., a photovoltaic device. In general, a radioactive material can be disposed within a sealed enclosure. A radiation particle converting material, e.g., phosphor, can be disposed within the enclosure. The particle converting material can be excited by the radiation particles emitted by the radioactive material. In one or more embodiments, the enclosure can be transparent to one or more wavelengths of the electromagnetic energy emitted by the particle converting material. Such energy can be incident upon an input surface of a photovoltaic device, where the device can be adapted to convert the electromagnetic radiation emitted by the particle converting material into electrical energy. The device can convert the electromagnetic radiation to electrical energy using any suitable technique or combination of techniques.

In one or more embodiments, the power source can utilize a single-step direct conversion, where the source includes a semiconductor junction. Radiation particles emitted by the radiation material are incident upon the semiconductor junction. The impact of these radiation particles on the semiconductor junction can create electron-hole pairs that can then be collected using any suitable technique or techniques.

One advantage of one or more of the embodiments of a power source described herein is that the conversion of radiation particles to electromagnetic radiation can provide high conversion efficiencies. Another advantage of one or more of the embodiments described herein is that the power source can allow for high volumetric conversion efficiency at a low cost. Further, one or more embodiments of power sources described herein can have a longevity that is equal to or greater than currently-available batteries.

The various embodiments of power sources described herein can be utilized with any suitable device or system. For example, in one or more embodiments, one or more of the power sources described herein can be utilized with any suitable implantable medical devices, e.g., electrocardiogram (ECG) monitors, sensors (such as glucose, pressure), implantable pulse generators (IPGs) (e.g., pacemakers), implantable cardioverter defibrillators (ICDs), etc. Further, for example, one or more of the described power sources can be utilized with electronic devices that are external to the human body, e.g., EKG sensors, ECG sensors, oxygen sensors, glucose sensors, hearing aids, etc.

FIG. 1 is a schematic cross-section view of one embodiment of a power source 10. The power source 10 includes an enclosure 12 and a substrate 20 disposed within the enclosure. The power source 10 also includes radioactive material 30 disposed within the substrate 20, and a diffusion barrier 40 disposed over an outer surface 22 of the substrate. Further, the power source 10 includes a carrier material 50 disposed within the enclosure 12. In one or more embodiments, the power source 10 can also include a converter 60. The converter 60 can be disposed within the enclosure 12, form a portion of the enclosure, or be disposed adjacent the enclosure as is further described herein. The converter 60 can be adapted to convert radioactive particles or radiation emitted by the particle converting material into electrical energy, e.g., electrical current. For example, in one or more embodiments, the converter 60 can include a photovoltaic device (e.g., photovoltaic device 260 of FIG. 4) that converts electromagnetic radiation emitted by particle converting material (e.g., particle converting material 270 of FIG. 4) disposed within the enclosure 12 when radioactive particles emitted by the radioactive material 30 are incident upon the particle converting material. Further, in one or more embodiments, the converter 60 can include a charge carrier separator (e.g., charge carrier separator 360 of FIG. 5) that converts radioactive particles emitted by radioactive material (e.g., radioactive material 330 of FIG. 5) that impact the charge carrier separator into electrical energy as is further described herein.

The enclosure 12 includes a housing 14 and a cover 16 connected to the housing. The housing 14 and the cover 16 can include any suitable material or combination of materials. For example, at least one of the housing 14 and cover 16 can include at least one of glass (e.g., borosilicate glass (BSG), photo-imageable glasses (e.g., FOTURAN® or APEX®), soda lime glass), ceramic, sapphire, silicon, gallium nitride (GaN), and other semiconductor materials (indium gallium arsenide, gallium arsenide), metals (e.g., titanium, stainless steel, copper, palladium, silver), etc. In one or more embodiments, at least one of the housing 14 and cover 16 can include one or more materials that are transparent to one or more wavelengths of electromagnetic radiation as is further described herein. For example, the housing 14 can include a reflective material or a transparent material. Further, in one or more embodiments, the cover 16 can include a reflective material or a transparent material. The housing 14 and the cover 16 can include the same material or materials. In one or more embodiments, the housing 14 includes materials that are different from the materials utilized to form the cover 16.

The enclosure 12 can take any suitable shape or combination of shapes and include any suitable dimensions. Further, the cover 16 can be connected to the housing 14 using any suitable technique or combination of techniques, e.g., welding, adhering, mechanically fastening, soldering, wafer bonding such as thermosonic or anodic bonding, etc. In one or more embodiments, the cover 16 is hermetically sealed to the housing 14 using any suitable technique or techniques. For example, the cover 16 can be hermetically sealed to the housing 14 by forming a laser bond between the cover and the housing as described, e.g., in co-owned U.S. Patent Application No. 62/096,706 (Medtronic Reference No. C00008775.USP1), entitled KINETICALLY LIMITED NANO-SCALE DIFFUSION BOND STRUCTURES AND METHODS.

The substrate 20 having the radioactive material 30 disposed therein, the diffusion barrier 40, and the carrier material 50 can be disposed within the housing 14, which can be hermetically sealed utilizing the cover 16 that is connected to the housing. In one or more embodiments, a vacuum can be created within the enclosure 12 prior to connecting the cover 16 to the housing 14 such that a near vacuum environment exists within the enclosure 12.

In one or more embodiments, the power source 10 can be constructed utilizing materials that are hermetic to, e.g., tritium oxide, but allow a product of the decay of the radioactive material 30, e.g., $^3$He (helium), to escape. For example, at least one of the housing 14 and the cover 16 can include borosilicate glass, soda lime glass, or similar materials that are known to allow for helium to diffuse therethrough. In one or more embodiments, at least one of the housing 14 and the cover 16 can be designed such that the power source 10 can tolerate a pressure buildup due to the production of the decay product, e.g., the housing 14 can include a volume that is large enough to contain the decay product. These mechanisms can eliminate or reduce pressure build-up within the enclosure 12 or reduce the need to increase the volume of the enclosure to contain the gaseous species produced during radioactive decay.

Although not shown in FIG. 1, the enclosure 12 can include one or more openings disposed through one or both of the housing 14 and the cover 16 that can provide access to an interior of the housing. For example, in one or more embodiments, one or more feedthroughs can be formed in one or both of the housing 14 and cover 16 that can provide electrical connections between devices or components disposed within the enclosure and devices or components disposed exterior to the enclosure. Further, in one or more embodiments, one or more ports can be formed in the enclosure 12 to provide fluid access to the interior of the enclosure for providing, e.g., gas or fluid ingress or egress.

Disposed within the enclosure 12 is the substrate 20. The substrate 20 can include any suitable material or combination of materials. In one or more embodiments, the materials of the substrate 20 can be selected such that the substrate can contain the radioactive material 30 until such time as an input or inputs can be provided to cause release or diffusion of at least a portion of the radioactive material from the substrate. Suitable materials for the substrate 20 include, e.g., palladium, uranium, or other material where the radioactive material is stored interstitially or using a weak atomic bond. In one or more embodiments, the substrate 20 is a metal substrate.

Further, the substrate 20 can take any suitable shape or combination of shapes and have any suitable dimensions. In one or more embodiments, the substrate 20 can form a portion or portions of at least one of the housing 14 and the cover 16. Although depicted as including a single substrate 20, the power source 10 can include any suitable number of substrates.

The power source 10 also includes the radioactive material 30. The radioactive material 30 can be any suitable material that emits one or more radiation particles. For example, in one or more embodiments, the radioactive material 30 can include the radioisotope tritium ($^3$H). Further, the radioactive material 30 can be in any suitable form, e.g., gas, liquid, solid, powder dispersed into a liquid/solid phase, etc. The radioactive material 30 can emit any suitable type of particles, e.g., alpha, beta, gamma, x-ray, etc.

The radioactive material 30 may also be introduced in one form, such as a gas phase, and then be in situ converted into a vapor, liquid or sold phase as it reacts with the carrier material 50. For example, tritium can be introduced in a gaseous phase, with the substrate 20 being titanium or palladium. The tritium is absorbed into the substrate 20 and converted into a solid phase, or as a gas dissolved within a solid (if no chemical bonding occurs), potentially allowing for a much higher tritium-per-volume concentration. In one or more embodiments, gaseous tritium can be introduced into the substrate 20 such that the tritium is stored in a solid phase, and an input such as an increase in temperature can be provided to the substrate such that at least a portion of the tritium diffuses or out-gases from the substrate. The gas phase of the tritium can be incident on the carrier material 50 and reduce the carrier material such that a liquid or vapor phase of the tritium (tritium oxide) is formed. Such liquid or vapor phase of the radioactive material 30 can have a higher tritium-per-volume density than the gaseous or solid phase of the tritium.

The radioactive material 30 can be disposed within the substrate 20 using any suitable technique or combination of techniques. For example, FIG. 2 is a flowchart of one embodiment 100 of a method of forming the substrate 30. Although described in reference to the substrate 30 of power source 10 of FIG. 1, the method 100 can be utilized to form any suitable substrate that includes a radioactive material disposed therein. At 102, the diffusion barrier 40 is disposed over the outer surface 22 of the substrate 20 using any suitable technique or techniques, e.g., sputtering. The substrate 20 is exposed to a gas phase of the radioactive material 30 at 104, e.g., a tritium gas. For example, the substrate 20 can be placed in a deposition chamber, and a source gas can be disposed within the chamber. At 106, at least one of a temperature of the substrate 20 and the pressure within the deposition chamber can be increased so that the source gas can penetrate the diffusion barrier 40 and the substrate 30. In one or more embodiments, the temperature of the source gas can be at least about 100 degrees C. In one or more embodiments, the source gas can be no greater than about 500 degrees C. Further, in one or more embodiments, the source gas can be at a pressure of at least about 10 mBar. In one or more embodiments, the source gas can be at a pressure of no greater than about 10 Bar. The radioactive material 30 is stored within the substrate 20 in the solid phase or as a gas contained within a solid until an input or inputs are provided to the substrate such that at least a portion of the radioactive material diffuses from the substrate.

The power source 10 also includes the diffusion barrier 40 disposed over the outer surface 22 of the substrate 20. In one or more embodiments, the diffusion barrier 40 can prevent at least a portion of the radioactive material 30 disposed within the substrate 20 from diffusing out of the substrate until the selected input is provided to the substrate. The diffusion barrier 40 can include any suitable material or materials, e.g., titanium, titanium dioxide (TiO$_2$), zirconium, zirconium dioxide (ZrO$_2$), magnesium, magnesium oxide (MgO), etc. The diffusion barrier 40 can include any suitable number of layers, e.g., one, two, three, or more layers. Each layer of the diffusion barrier 40 can include the same materials. In one or more embodiments, one layer of the diffusion barrier 40 can include a material or materials that are different from the material or materials of one or more additional layers of the diffusion barrier.

Further, the diffusion barrier 40 can be disposed over any suitable portion or portions of the outer surface 22 of the substrate 20. In one or more embodiments, the diffusion barrier 40 is disposed over the entire outer surface 22 of the substrate 20. The diffusion barrier 40 can be disposed using any suitable technique or combination of techniques, e.g., sputtering, evaporation, ALD, e-beam evaporation, plating. In one or more embodiments, the diffusion barrier 40 can be in contact with the outer surface 22 of the substrate 20. In one or more embodiments, one or more additional layers (e.g., an adhesive or bonding layer) can be disposed between the diffusion barrier 40 and the outer surface 22.

Further, the diffusion barrier 40 can have any suitable thickness. In one or more embodiments, the diffusion barrier 40 has an average thickness of at least about 10 nm. In one or more embodiments, the diffusion barrier 40 has an average thickness of no greater than about 50 nm.

As mentioned herein, the power source 10 also includes the carrier material 50. In one or more embodiments, the carrier material 50 can be utilized to change the phase of the radioactive material 30 from the solid phase or as a gas contained within a solid to either the liquid, vapor or solid phase using any suitable mechanism. For example, in one or more embodiments, the radioactive material 30 can be tritium in a solid phase or as a gas contained within a solid stored within the substrate 20, and the carrier material 50 can include an oxide material such as palladium oxide (PdO). The substrate 20 can be heated such that the tritium diffuses from the substrate and reduces the palladium oxide, thereby generating palladium and tritium oxide.

The carrier material 50 can include any suitable material or materials to provide an oxygen source for the radioactive material 30, e.g., palladium oxide, silver oxide, mercury oxide, or combinations thereof. In one or more embodiments, the carrier material 50 can be selected such that it readily reduces the radioactive material 30 that has diffused from the substrate 20 at temperatures around the same as, less than, or higher than the temperature that is required to liberate the radioactive material from the substrate.

The carrier material 50 can be disposed in any suitable location within the enclosure 12. In one or more embodiments, the carrier material 50 can be disposed on the substrate 20. For example, the carrier material 50 can be disposed on the diffusion barrier 40. In one or more embodiments, the carrier material 50 can be disposed within the enclosure 12 such that it is spaced apart from the substrate 20.

The carrier material 50 can be provided in any suitable form. For example, in one or more embodiments, the carrier material 50 can be a layer or layers that are disposed, e.g., on the diffusion barrier 40 using any suitable technique or techniques. Further, in one or more embodiments, the carrier material 50 can be in the form of one or more particles that are disposed within the enclosure 12 using any suitable technique or techniques. For example, the carrier material 50 can be provided as a powder that may be dispersed or deposited within the enclosure 12. In one or more embodiments, the carrier material 50 can be in the form of pellets or slugs that are disposed within the enclosure 12. In one or more embodiments, the carrier material 50 can be provided as a solid material that has a structure having a high surface area and a low volume, e.g., a foam, a mesh, etc.

In the embodiment illustrated in FIG. 1, the power source 10 can be stored for any suitable period of time as the radioactive material 30 remains disposed within the substrate 20 and separated from the carrier material 50 by the diffusion barrier 40. At the desired time, the power source 10 can be activated to provide radioactive particles within the enclosure 12 using any suitable technique or techniques. In one or more embodiments, the substrate 20 can be heated to a selected temperature such that the radioactive material 30 can diffuse from the substrate 20 and react with the carrier material 50 using any suitable technique or techniques. In one or more embodiments, a pressure within the enclosure 12 can be increased such that the radioactive material 30 diffuses from the substrate 20 and diffusion barrier 40. Further, in one or more embodiments, both the temperature of the substrate 20 and the pressure within the enclosure 12 can be decreased such that the radioactive material 30 diffuses from the substrate and the diffusion barrier 40.

The substrate 20 that includes the radioactive material 30 disposed therein can be utilized with any suitable power source or sources. As shown in FIG. 1, the substrate 20 can be included in the power source 10 within the enclosure 12. Such substrate 20 can be disposed within the enclosure and utilized to produce radioactive particles using any suitable technique or techniques. For example, FIG. 3 is a flow chart of one embodiment 110 of a method of forming the power source 10. Although described in reference to the power source 10 of FIG. 1, the method 110 can be utilized to provide any suitable power source. At 112, the substrate 20 including the radioactive material 30 and the diffusion barrier 40 is disposed within the housing 14 of the power source 10. The substrate 20 can be disposed in any suitable location within the housing 14. In one or more embodiments, the substrate 20 can be connected to one or more side walls of an inner surface 15 of the housing using any suitable technique or techniques. At 114, the carrier material 50 is disposed within the housing 14 using any suitable technique or techniques. For example, in one or more embodiments, the carrier material 50 is disposed within the housing 14 as a solid layer of material on the diffusion barrier 40 of the substrate 20.

The housing 14 can be sealed with the cover 16 by connecting the cover to the housing using any suitable technique or techniques at 116. Prior to sealing the cover 16 to the housing 14, a vacuum can be created within the housing using any suitable technique or techniques. At 118, an input can be provided to the substrate 20 (e.g., the substrate 20 can be heated using any suitable technique or techniques) such that at least a portion of the radioactive material 30 diffuses from the substrate and diffusion barrier 40 and reacts with the carrier material 50 to form a liquid, vapor, or solid phase of the radioactive material that is adapted to produce one or more radioactive particles. For example, in one or more embodiments, heating of the substrate 20 causes tritium to diffuse from the substrate and diffusion barrier 40 and react with an oxide carrier material 50 to form tritium oxide within the enclosure 12.

Figure 4:
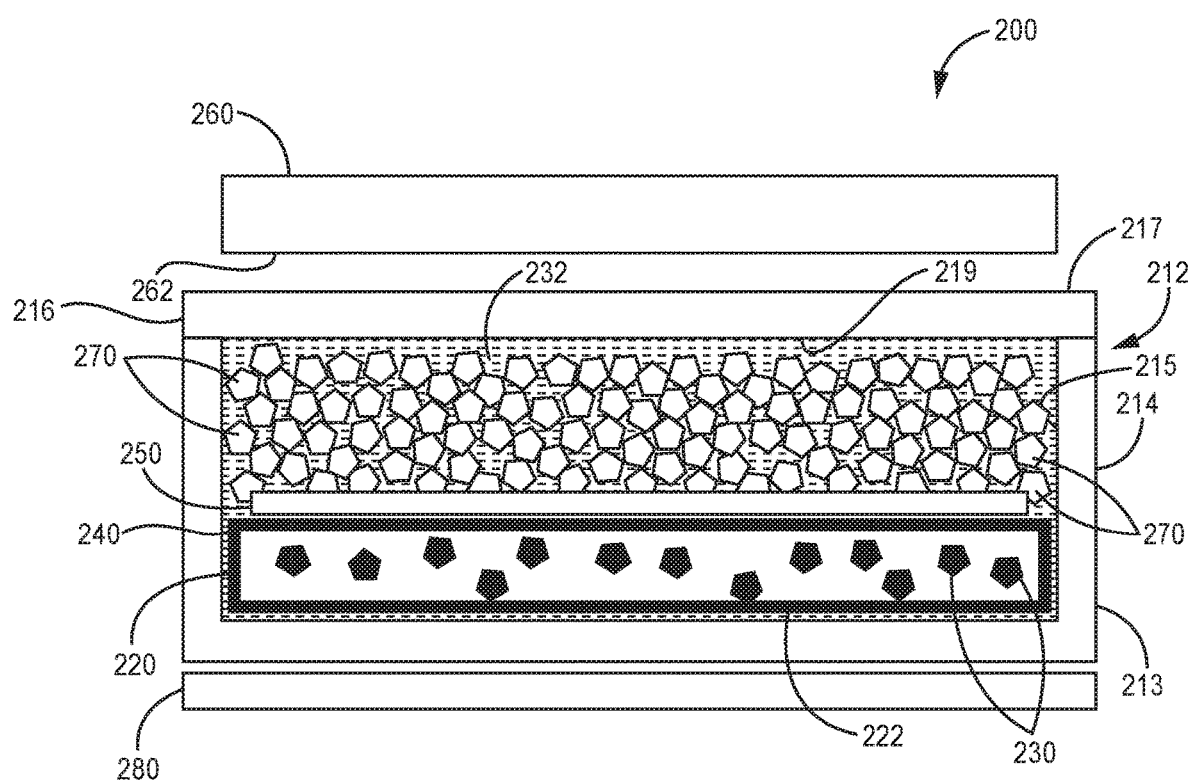
FIG. 4 is a schematic cross-section view of another embodiment of a power source.

Returning to FIG. 1, the power source 10 includes the radioactive particle converter 60. The converter 60 can include any suitable component or system that is adapted to convert one or more radioactive particles emitted by the radioactive material 30 after at least a portion of such material diffuses from the substrate 20 and diffusion barrier 40 and reacts with the carrier material 50. For example, FIG. 4 is a schematic cross-section view of another embodiment of a power source 200. All of the design considerations and possibilities regarding the power source 10 of FIG. 1 apply equally to the power source 200 of FIG. 4.

The power source 200 includes an enclosure 212 having a housing 214 and a cover 216 connected to the housing. In one or more embodiments, the cover 216 is sealed to the housing 214. Further, in one or more embodiments, the cover 216 is hermetically sealed to the housing 214.

The power source 200 also includes a substrate 220 disposed within the enclosure 212.

The substrate 220 can include radioactive material 230 disposed therein as described regarding substrate 20 of FIG. 1. In one or more embodiments, the power source 200 can also include a diffusion barrier 240 disposed over the substrate 220.

The power source 200 can also include a carrier material 250 disposed within the housing 214. As described herein, an input or inputs can be provided to the substrate 220 such that at least a portion of the radioactive material 230 disposed within the substrate diffuses out of the substrate and the diffusion barrier 40 and reacts with the carrier material 250 to provide a liquid, vapor, or solid phase of the radioactive material. In the embodiment illustrate in FIG. 4, a portion of the radioactive material 230 has diffused from the substrate 220 and reacted with the carrier material 250 to form a liquid phase 232 of the radioactive material that at least partially fills the enclosure 212.

Also disposed within the housing 214 is particle converting material 270. The particle converting material 270 is adapted to convert radioactive particles emitted by the liquid phase radioactive material 232 (and the solid or gas phase radioactive material 230) into electromagnetic radiation, e.g., light. The particle converting material 270 can include any suitable material or combination of materials, e.g., one or more of phosphor, ZnS:Ag, ZnS:Mn, ZnO:Zn, (Zn, Cd)S:Cu, $Y_2O_3S$:Eu, $Y_2O_3$:Eu, $Y_2O_3$:Er, $YVO_4$:Eu, $YVO_4$:Er. The particle converting material can have coating deposited on its surface to passivate the defects reducing their propagation by the impact energy of the radiation particle onto the particle converting material. The deposition of the passivation layer can be achieved using ALD or other suitable methodologies. The passivation layer may consist of alumina ($Al_2O_2$), silicon dioxide ($SiO_2$) or other suitable material that has the ability to passivate the surface.

In one or more embodiments, the particle converting material 270 can include nanocrystals. As used herein, the term "nanocrystal" refers to nanostructures that are substantially monocrystalline. A nanocrystal has at least one region or characteristic dimension with a dimension of less than about 500 nm, and down to on the order of less than about 1 nm. The terms "nanocrystal," "nanodot," "dot," and "quantum dot" are readily understood by the ordinarily skilled artisan to represent like structures and are used herein interchangeably. The present disclosure also encompasses the use of polycrystalline or amorphous nanocrystals. Typically, the region of characteristic dimension will be along the smallest axis of the structure. Nanocrystals can be substantially homogenous in material properties, or in some embodiments, can be heterogeneous.

The nanocrystals can be produced using any suitable technique or techniques. The nanocrystals for use in the present disclosure can also include any suitable material or materials, including an inorganic material, and more suitably an inorganic conductive or semiconductive material. Suitable semiconductor materials can include any type of semiconductor, including group II-VI, group III-V, group IV-VI and group IV semiconductors. Suitable semiconductor materials can include, but are not limited to, Si, Ge, Sn, Se, Te, B, C (including diamond), P, BN, BP, BAs, AlN, AlP, AlAs, AlSb, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and combinations thereof.

In one or more embodiments, the semiconductor nanocrystals can include a dopant such as a p-type dopant or an n-type dopant. The nanocrystals useful in the present disclosure can also include II-VI or III-V semiconductors. Examples of II-VI or III-V semiconductor nanocrystals include any combination of an element from Group II, such as Zn, Cd and Hg, with any element from Group VI, such as S, Se, Te, Po, of the Periodic Table; and any combination of an element from Group III, such as B, Al, Ga, In, and Tl, with any element from Group V, such as N, P, As, Sb and Bi, of the Periodic Table.

In one or more embodiments, the nanocrystals can include core-shell structures that are obtained by adding organometallic precursors containing the shell materials to a reaction mixture containing the core nanocrystal. In this case, rather than a nucleation-event followed by growth, the cores act as the nuclei, and the shells grow from their surfaces. The temperature of the reaction is kept low to favor the addition of shell material monomers to the core surface, while preventing independent nucleation of nanocrystals of the shell materials. Surfactants in the reaction mixture are present to direct the controlled growth of shell material and ensure solubility. A uniform and epitaxially grown shell is obtained when there is a low lattice mismatch between the two materials.

Exemplary materials for preparing core-shell nanocrystals can include, but are not limited to, Si, Ge, Sn, Se, Te, B, C (including diamond), P, Co, Au, BN, BP, BAs, AlN, AlP, AlAs, AlSb, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and combinations thereof. Exemplary core-shell luminescent nanocrystals include, but are not limited to, (represented as Core/Shell), CdSe/ZnS, InP/ZnS, PbSe/PbS, CdSe/CdS, CdTe/CdS, CdTe/ZnS, as well as others.

The material utilized for the particle converting material 270 can be selected such that the material emits electromagnetic radiation at any desired wavelength or within any desired wavelength range. For example, in one or more embodiments, the particle converting material 270 is adapted such that it emits electromagnetic radiation in the visible spectrum, i.e., visible light. In one or more embodiments, the particle converting material 270 can be selected such that it emits light in the UV, infrared, or near-infrared wavelength range. The particle converting material 270 can be selected such that it emits light at a single wavelength, two or more discrete wavelengths, or a range of wavelengths, e.g., 190 nm to 450 nm, 364 nm to 640 nm, or 530 nm to 2000 nm. The specific wavelength used is an optimization of the conversion of radioactive particles to electromagnetic radiation and the associated photovoltaic device's light-to-electric-power-conversion efficiency.

The particle converting material 270 can be disposed in any suitable location within the housing 214. In one or more embodiments, the particle converting material 270 can be disposed on one or more portions of an inner surface 215 of the housing 214. In one or more embodiments, the particle converting material 270 can be disposed on an inner surface 219 of the cover 216. In one or more embodiments, the particle converting material 270 can be disposed within the liquid phase radioactive material 232.

The power source 200 also includes a photovoltaic device 260. The photovoltaic device 260 can be disposed in any suitable location either within the enclosure 212 or adjacent to the enclosure. As used herein, the term "adjacent the enclosure" means that the photovoltaic device is disposed in relation to the enclosure 212 such that at least a portion of electromagnetic radiation emitted by the particle converting material 270 disposed within the enclosure is incident upon an input surface 262 of the photovoltaic device. In one or more embodiments, the input surface 262 of the photovoltaic device 260 can be disposed on an outer surface 213 of the housing 214 or an outer surface 217 of the cover 216. Further, in one or more embodiments, the photovoltaic device 260 can form at least a portion of the enclosure 212, e.g., the input surface 262 of the device can form a portion or portions of at least one of the housing 214 and the cover 216.

The photovoltaic device 260 can include any suitable device that is adapted to convert at least a portion of the electromagnetic radiation emitted by the particle converting material 270 into electrical energy, e.g., current. For example, the photovoltaic device 260 can include at least one of a photodiode, pn junction, p-i-n junction, or multi-layered multi junction photon convertor, which include Si, Ge, SiGe, GaN, GaAs, AlGaAs, InGaP, GaP, SiC, etc. The photovoltaic device 260 can be adapted to convert any suitable wavelength or range of wavelengths of electromagnetic radiation emitted by the particle converting material 270 into electrical energy. Further, the photovoltaic device 260 can be electrically connected to one or more electronic devices using any suitable technique or combination of techniques to provide electrical energy to the electronic devices.

In one or more embodiments, the power source 200 can provide electrical energy to one or more electronic devices that is electrically connected to the power source. For example, in one or more embodiments, the liquid phase radioactive material 232 can emit one or more radioactive particles, e.g., beta particles. One or more of these beta particles can be incident upon the particle converting material 270, which can convert one or more of these beta particles into electromagnetic radiation, e.g., light. At least a portion of the electromagnetic radiation emitted by the particle converting material 270 can be incident upon the input surface 262 of the photovoltaic device 260. The device 260 can convert at least a portion of the electromagnetic radiation incident upon the input surface 262 into electrical energy. This electrical energy can then be directed to one or more electronic devices that are electrically connected to the photovoltaic device 260.

The power source 200 can include an additional layer or layers 280 that can provide additional functionality to the source. For example, in one or more embodiments, the additional layer 280 can include a reflective layer or layers disposed either within the enclosure 212 or external to the enclosure that can direct incident electromagnetic radiation emitted by the particle converting material 270 to the input surface 262 of the photovoltaic device 260. The reflective layer can include any suitable material or combination of materials, e.g., metal, polymeric, metallic oxides, metallic nitrides, etc. The reflective layer can be formed using any suitable technique or combination of techniques.

Further, the additional layer 280 can include an anti-reflective layer that can prevent the reflection of the electromagnetic radiation, e.g. light, back into the enclosure 212. The anti-reflection layer can be disposed in any suitable location within the enclosure 212 or external to the enclosure. The anti-reflection layer 280 can include any suitable material or combination of materials, e.g., metallic oxides, metallic nitrides (e.g., TiN, $TiO_2$ etc.), and combinations thereof. Further, the anti-reflection layer can be formed using any suitable technique or combination of techniques, e.g., ALD, MOCVD, sputtering, evaporation, plating, etc.

Figure 5:
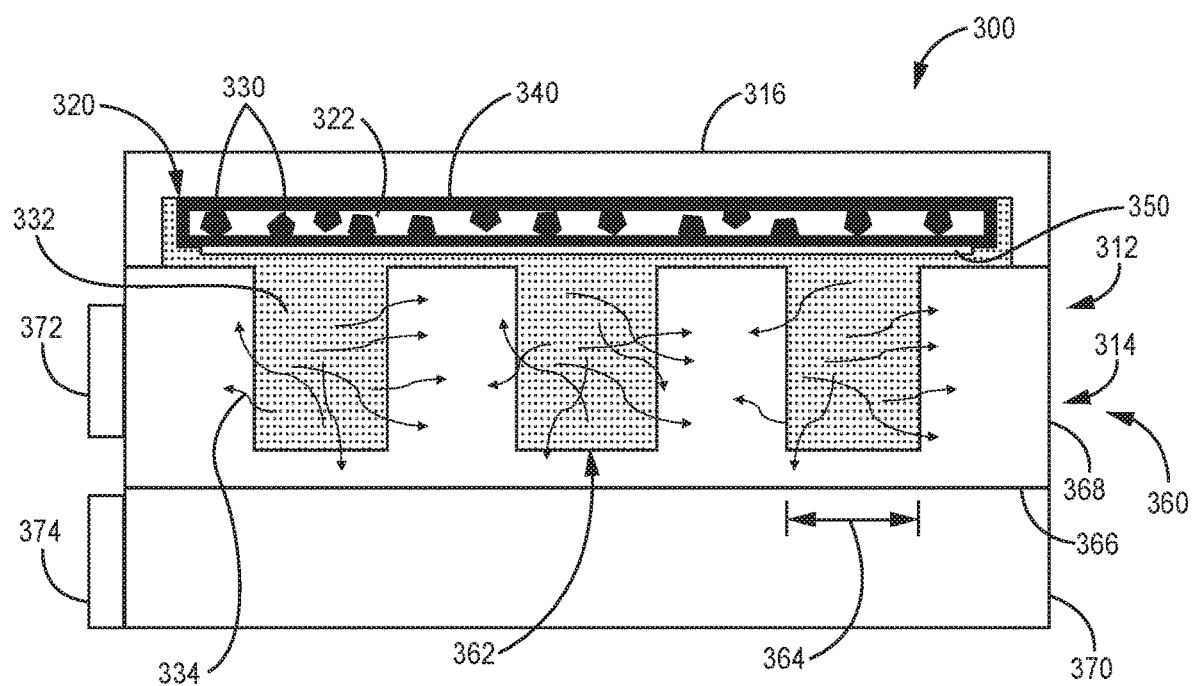
FIG. 5 is a schematic cross-section view of another embodiment of a power source.

As mentioned herein, one or more radioactive particles emitted by radioactive material can be directly converted to electrical energy utilizing any suitable semiconductor junction. For example, FIG. 5 is a schematic cross-section view of another embodiment of a power source 300. All of the design considerations and possibilities regarding the power source 10 of FIG. 1 apply equally to the power source 300 of FIG. 5.

The power source 300 includes an enclosure 312 having a housing 314 and a cover 316 connected to the housing such that the enclosure is hermetically sealed. The power source 300 also includes a substrate 320 that includes a diffusion barrier layer 340 disposed over an outer surface 322 of the substrate. Radioactive material 330 can be disposed within the substrate 320. The radioactive material 330 is adapted to emit radioactive particles 334. The power source 300 can also include carrier material 350 disposed within the housing 314 in any suitable location. An input or inputs can be provided to the substrate 320 such that at least a portion of the radioactive material disposed therein can diffuse from the substrate and the diffusion barrier 340 and react with the carrier material 350 to provide a liquid, vapor, or solid phase 332 of the radioactive material. As shown in FIG. 5, the power source 300 includes the liquid phase radioactive material 332.

One difference between the power source 10 of FIG. 1 and the power source 300 of FIG. 5 is that the power source 300 includes a charge carrier separator 360 disposed within the housing as a particle converter (e.g., particle converter 60 of FIG. 1). In one or more embodiments, the charge carrier separator 360 is disposed within the housing 312 such that radioactive particles 334 emitted by the liquid phase radioactive material 332 are incident upon the charge carrier separator.

In one or more embodiments, the radioactive material 330 disposed within the substrate 320 can be in a solid phase or as a gas contained within a solid. At least a portion of the radioactive material 330 can diffuse out of the substrate 320 and diffusion barrier 340 as described herein and react with the carrier material 350 disposed within the housing 314 to provide radioactive material in the liquid phase 332. The liquid phase radioactive material 332 can be disposed in any suitable location within the housing 314. In one or more embodiments, the liquid phase radioactive material 332 can be disposed within one or more wells 362 that are disposed in the charge carrier separator 360.

The wells 362 in the charge carrier separator 360 can take any suitable shape or combination of shapes and have any suitable dimensions. In one or more embodiments, a width 364 of one or more wells 362 can be no greater than ten times a mean free path of the radioactive particles 334 emitted by the liquid phase radioactive material 332.

The charge carrier separator 360 can include any suitable charge carrier separator and be disposed in any suitable location. For example, as illustrated in FIG. 5, the charge carrier separator 360 forms at least a portion of the housing 314. In one or more embodiments, the charge carrier separator 360 forms the entire housing 314 such that the cover 316 is connected to the charge carrier separator to provide a hermetically-sealed enclosure 312.

The charge carrier separator 360 can include any suitable material or materials. In one or more embodiments, the separator 360 can include an oxide. In one or more embodiments, the charge carrier separator 360 can include nanocrystals, e.g., the same nanocrystals described herein regarding the particle converting material 270 of power source 200 of FIG. 4.

In one or more embodiments, the charge carrier separator 360 can include other types of structures, e.g., quantum wells, PN junctions, PIN junctions, schottky junctions, and perovskite structures. And in one or more embodiments, the charge carrier separator 360 can include two or more types of materials, e.g., an oxide layer combined with nanocrystals, two or more different types of nanocrystals, one or more quantum wells combined with nanocrystals, etc., as is further described herein.

As illustrated in FIG. 5, the charge carrier separator 360 includes a pn junction 366 formed by a p-type material 368 and an n-type material 370. The p-type material 368 can include any suitable type of intrinsic p-type semiconductor or doped semiconductor materials Semiconductor materials can include, but are not limited to, Si, Ge, Sn, Se, Te, B, C (including diamond), P, BN, BP, BAs, AlN, AlP, AlAs, AlSb, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, Pb Se, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and combinations thereof.

Further, the n-type material 370 can include any suitable type of semiconductor material or materials, e.g., the same materials described herein regarding the p-type materials. The terms "n-doped" or "n-type" as they are used in this disclosure refer to a semiconductor material that includes a dopant that provides for excess electrons to act as negative, or "n-type," mobile charge carriers. In one example, an n-type dopant can donate one or more valence electrons to a semiconductor material. The n-type semiconductor material may also be made of intrinsic n-type material.

The charge carrier separator 360 also includes first and second electrodes 372, 374 that are electrically connected to the p-type material 368 and the n-type material 370 respectively. The first and second electrodes 372, 374 can take any suitable shape or shapes and include any suitable materials, e.g., metals, conductive polymers, other suitable electrical conductors, or combinations thereof. In one or more embodiments, the first and second electrodes 372, 374 can electrically couple the power source 300 to other devices using any suitable techniques. Further, either of the first or second electrodes 372, 374 can be positive or negative depending upon the application in which the power source 300 is utilized.

The power source 300 can include any suitable additional layer or layers. For example, although not shown, the charge carrier separator 360 can also include a three-dimensional current collector that can take any suitable shape or shapes and be disposed in any suitable location relative to the PN junction 366. Such three-dimensional current collector can include nano rods, nanotubes, nano wires, nanocrystalline structures, metal foam, graphene foam, and combinations thereof. In one or more embodiments, the collector can include a lithographically-patterned structure or other ordered structure such as those that can be manufactured using, e.g., 3D printing techniques. And the surface of the collector can take any suitable shape or shapes. In general, the three-dimensional current collector can, in one or more embodiments, maximize a surface area of surface for any given volume. The hole conductor layer can include any suitable material or materials. For example, in one or more embodiments, the hole conductor layer can include any suitable p-type semiconductor material.

The power source 300 can also include a hole conductor layer disposed in a suitable location relative to the PN junction 366. In one or more embodiments, the power source 300 can include optional counter electrode disposed between the hole conductor layer and second electrode. The counter electrode can be electrically coupled to the hole conductor layer. In one or more embodiments, the counter electrode can electrically couple the hole conductor layer and the second electrode 374. In one or more embodiments, the counter electrode can be in contact with the second electrode 374. In one or more embodiments, the counter electrode can be electrically coupled to the second electrode 374 through a conductive adhesive. Further, in one or more embodiments, the counter electrode can be electrically coupled to the hole conductor layer through a conductive adhesive (not shown). And in one or more embodiments, the counter electrode can serve as the second electrode, thereby replacing second electrode 374.

The counter electrode can include any suitable material or materials, e.g., Au, Pt, graphene, a metallic material, a conducting polymer, a semiconductor, or combinations thereof.

The power source 300 can include any other suitable layer or layers. For example, in one or more embodiments, the power source 300 can include one or more absorption layers for absorbing radioactive particles that are emitted by the radioactive material 330 and the liquid phase radioactive material 332 to prevent the release of radioactive particles from the power source. Such one or more absorbing layers may also absorb bremsstrahlung (x-rays) resulting from the deceleration of radioactive particles emitted by the radioactive materials 330, 332.

Figure 6:
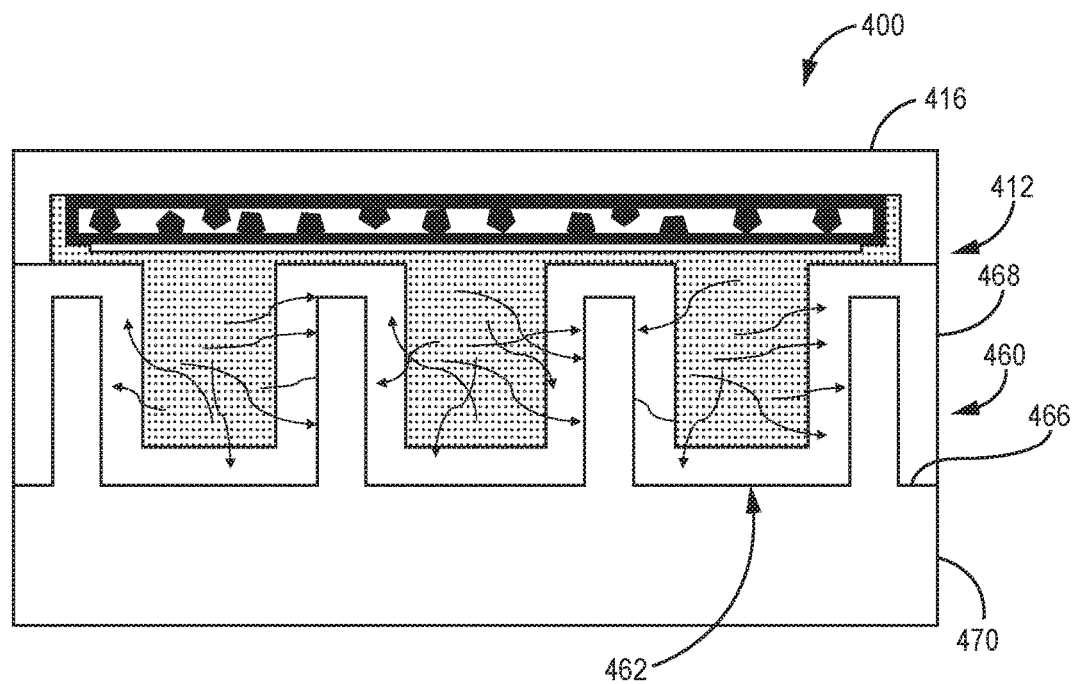
FIG. 6 is a schematic cross-section view of another embodiment of a power source.

FIG. 6 is another embodiment of a power source 400. All of the design considerations and possibilities regarding the power source 300 of FIG. 5 apply equally to the power source 400 of FIG. 6. One difference between the power source 400 and the power source 300 is that a charge carrier separator 460 of power source 400 includes a conformal pn junction 466 that forms one or more wells 462. As illustrated in FIG. 6, a p-type material 468 is disposed on an n-type material 470 such that the wells are formed by both the p- and n-type materials. The wells 462 can take any suitable shape or combination of shapes. Further, the power source 400 can include any suitable number of wells. The charge carrier separator 460 forms a housing 414 of enclosure 412. A cover 416 can be connected to the housing 414 such that the enclosure 412 is hermetically sealed.

Figure 7:
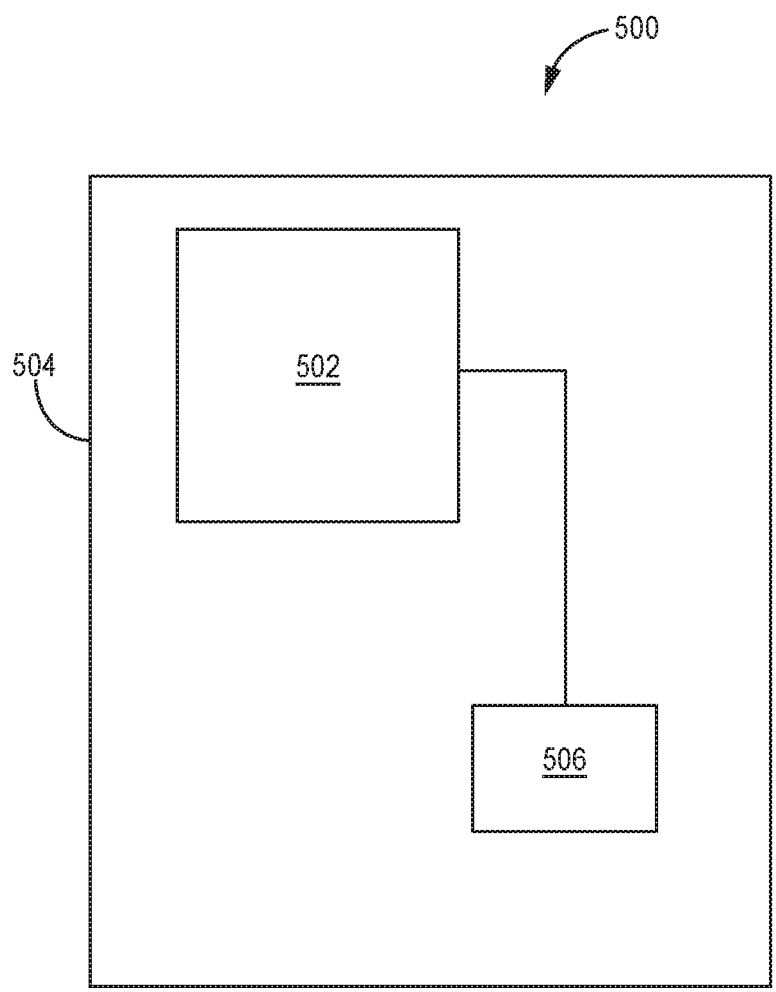
FIG. 7 is a schematic cross-section view of an implantable medical device that includes a power source.

The various embodiments of power sources described herein can be utilized to provide electrical energy to any suitable electronic devices or circuitry. For example, FIG. 7 is a schematic cross-section view of one embodiment of an implantable medical device 500. The implantable medical device 500 can include a power source 502 disposed within an enclosure 504 of the device. Any suitable power source or combination of power sources can be disposed within the enclosure 504, e.g., power source 10 of FIG. 1. The power source 502 can be electrically connected to one or more electronic devices 506 disposed within the enclosure 504.

The one or more electronic devices 506 can include any suitable devices, components, or circuitry, e.g., ECG sensors, EKG sensors, glucose sensors, chemical sensors, biomarker sensors, power/voltage converters (e.g., stepping up or down voltage), accumulators (e.g., to store energy to be used for peak power demands, such as telemetry or therapy), electrocardiogram (ECG) monitors, implantable pulse generators (IPGs) (e.g., pacemakers), implantable cardioverter defibrillators (ICDs), etc.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A power source, comprising:
    an enclosure comprising a housing and a cover connected to the housing such that the enclosure is hermetically sealed;
    a substrate disposed within the enclosure;
    radioactive material disposed within the substrate and adapted to emit radioactive particles;
    a carrier material disposed within the housing, wherein the carrier material is adapted to change a phase of the radioactive material that has diffused from the substrate and is incident upon the carrier material;
    particle converting material disposed within the housing, wherein the particle converting material is adapted to convert the radioactive particles emitted by the radioactive material into light; and
    a photovoltaic device disposed adjacent the enclosure, wherein the photovoltaic device converts at least a portion of the light emitted by the particle converting material that is incident upon an input surface of the photovoltaic device into electrical energy.

2. The power source of claim 1, wherein the particle converting material comprises phosphor.

3. The power source of claim 1, wherein the housing comprises a reflective material and the cover comprises a transparent material.

4. The power source of claim 1, wherein the radioactive material is in a liquid phase when the radioactive material diffuses from the substrate and reacts with the carrier material.

5. The power source of claim 1, wherein the radioactive material comprises tritium and the carrier material comprises an oxide material.

6. The power source of claim 1, further comprising a reflective layer disposed on an inner surface of the housing.

7. The power source of claim 1, wherein at least one of the housing and the cover comprises a glass material.

8. The power source of claim 1, wherein the particle converting material comprises nanocrystals.

9. The power source of claim 1, wherein the particle converting material is disposed on one or more portions of an inner surface of the housing.

10. The power source of claim 1, wherein the particle converting material is disposed on an inner surface of the cover.

11. The power source of claim 1, wherein an input surface of the photovoltaic device is disposed on an outer surface of the housing.

12. The power source of claim 1, wherein an input surface of the photovoltaic device is disposed on an outer surface of the cover.

13. An implantable medical device comprising:
a device enclosure;
a power source disposed within the device enclosure, wherein the power source comprises:
  a power source enclosure;
  a substrate disposed within the power source enclosure;
  radioactive material disposed within the substrate and adapted to emit radioactive particles;
  a diffusion barrier disposed over an outer surface of the substrate; and
  a carrier material disposed within the power source enclosure, wherein the carrier material comprises an oxide material, and further wherein the carrier material is adapted to change a phase of the radioactive material that has diffused from the substrate and is incident upon the carrier material; and
one or more electronic devices disposed within the device enclosure and electrically connected to the power source.

14. The device of claim 13, wherein the one or more electronic components comprises at least one of an ECG sensor, EKG sensor, glucose sensor, chemical sensor, or biomarker sensor.

15. The device of claim 13, wherein the one or more electronic components comprises at least one of a power/voltage converter or an accumulator.

16. The device of claim 13, wherein the one or more electronic components comprises at least one of an ECG monitor, implantable pulse generator, or implantable cardioverter defibrillator.

17. The device of claim 13, wherein the power source enclosure comprises a housing and a cover connected to the housing.

18. The device of claim 17, wherein the housing comprises a reflective material and the cover comprises a transparent material.

19. The device of claim 13, wherein the power source further comprises a photovoltaic device disposed adjacent the power source enclosure, wherein the photovoltaic device converts at least a portion of the light emitted by the particle converting material that is incident upon an input surface of the photovoltaic device into electrical energy.

20. The device of claim 13, wherein the radioactive material comprises tritium.

* * * * *